(12) United States Patent
Olson et al.

(10) Patent No.: US 10,433,929 B2
(45) Date of Patent: Oct. 8, 2019

(54) SYSTEM AND METHOD FOR LOCAL DEFORMABLE REGISTRATION OF A CATHETER NAVIGATION SYSTEM TO IMAGE DATA OR A MODEL

(75) Inventors: Eric S. Olson, Maplewood, MN (US); Eric J. Voth, Maplewood, MN (US); Jeffrey A. Schweitzer, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 2437 days.

(21) Appl. No.: 11/715,923

(22) Filed: Mar. 9, 2007

(65) Prior Publication Data
US 2008/0221425 A1 Sep. 11, 2008

(51) Int. Cl.
*A61B 90/00* (2016.01)
*A61B 34/20* (2016.01)
(Continued)

(52) U.S. Cl.
CPC .............. *A61B 90/36* (2016.02); *A61B 34/20* (2016.02); *A61B 34/10* (2016.02); *A61B 34/30* (2016.02);
(Continued)

(58) Field of Classification Search
CPC ........ A61B 19/5244; A61B 2019/5255; A61B 90/36; A61B 34/20
(Continued)

(56) References Cited

U.S. PATENT DOCUMENTS 5,297,549 A 3/1994 Beatty et al.
5,391,199 A 2/1995 Ben-Haim
(Continued)

FOREIGN PATENT DOCUMENTS

EP 1743575 1/2007
EP 1757227 2/2007
(Continued)

OTHER PUBLICATIONS

Jain et al., FTRAC—A robust fluoroscope tracking fiducial, Oct. 2005, Med. Phys., 32(10), pp. 3185-3198.*
(Continued)

*Primary Examiner* — Hien N Nguyen
(74) *Attorney, Agent, or Firm* — Wiley Rein LLP

(57) ABSTRACT

A method for registering a catheter navigation system to a three-dimensional image generally includes obtaining a three-dimensional image including position information for a plurality of surface points on a part of a patient's body, using a catheter navigation system to place a tool at a location on the surface of the patient's body, measuring position information for the surface location, identifying a corresponding location on the image, associating position information for the surface location and the location identified on the image as a fiducial pair, and using at least one fiducial pair to generate a mapping function. The mapping function transforms points within the coordinate system of the catheter navigation to the coordinate system of the three-dimensional image such that, for each fiducial pair, the mapping error is about zero. Suitable warping algorithms include thin plate splines, mean value coordinates, and radial basis function networks.

9 Claims, 4 Drawing Sheets

(51) Int. Cl.
*A61B 17/00* (2006.01)
*A61B 34/30* (2016.01)
*A61B 34/10* (2016.01)

(52) U.S. Cl.
CPC .............. *A61B 2017/00053* (2013.01); *A61B 2017/00243* (2013.01); *A61B 2017/00703* (2013.01); *A61B 2034/105* (2016.02); *A61B 2034/2051* (2016.02); *A61B 2034/2053* (2016.02); *A61B 2034/2072* (2016.02); *A61B 2034/301* (2016.02); *A61B 2090/364* (2016.02)

(58) Field of Classification Search
USPC ........................................................ 600/426
See application file for complete search history.

(56) References Cited

U.S. PATENT DOCUMENTS

| | | | |
|---|---|---|---|
| 5,480,422 | A | 1/1996 | Ben-Haim |
| 5,546,951 | A | 8/1996 | Ben-Haim |
| 5,568,809 | A | 10/1996 | Ben-Haim |
| 5,662,108 | A | 9/1997 | Budd et al. |
| 5,694,945 | A | 12/1997 | Ben-Haim |
| 5,697,337 | A | 12/1997 | Wittkampf |
| 5,697,377 | A | 12/1997 | Wittkampf |
| 5,718,241 | A | 2/1998 | Ben-Haim et al. |
| 5,738,096 | A | 4/1998 | Ben-Haim |
| 5,840,025 | A | 11/1998 | Ben-Haim |
| 5,944,022 | A | 8/1999 | Nardella et al. |
| 5,954,665 | A | 9/1999 | Ben-Haim |
| 5,983,126 | A | 11/1999 | Wittkampf |
| 6,016,439 | A * | 1/2000 | Acker ............................ 600/411 |
| 6,066,094 | A | 5/2000 | Ben-Haim |
| 6,104,944 | A | 8/2000 | Martinelli |
| 6,161,032 | A | 12/2000 | Acker |
| 6,226,542 | B1 | 5/2001 | Reisfeld |
| 6,468,265 | B1 | 10/2002 | Evans et al. |
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 2002/0115941 | A1 | 8/2002 | Whayne |
| 2002/0168618 | A1 | 11/2002 | Anderson et al. |
| 2003/0021381 | A1 | 1/2003 | Koppe |
| 2003/0053697 | A1 | 3/2003 | Aylward |
| 2003/0233037 | A1 | 12/2003 | Bencini |
| 2004/0097806 | A1* | 5/2004 | Hunter et al. ................. 600/434 |
| 2004/0138548 | A1* | 7/2004 | Strommer et al. ............ 600/407 |
| 2004/0254437 | A1 | 12/2004 | Hauck et al. |
| 2004/0258887 | A1* | 12/2004 | Maciag et al. ................. 428/156 |
| 2005/0080328 | A1 | 4/2005 | Vass et al. |
| 2005/0137478 | A1 | 6/2005 | Younge et al. |
| 2005/0197568 | A1 | 9/2005 | Vass et al. |
| 2005/0222554 | A1 | 10/2005 | Wallace et al. |
| 2005/0244042 | A1 | 11/2005 | Sirohey |
| 2006/0078195 | A1 | 4/2006 | Vaillant |
| 2006/0079759 | A1 | 4/2006 | Vaillant |
| 2006/0084867 | A1 | 4/2006 | Tremblay et al. |
| 2006/0095022 | A1 | 5/2006 | Moll et al. |
| 2006/0100610 | A1 | 5/2006 | Wallace et al. |
| 2006/0116575 | A1 | 6/2006 | Willis |
| 2006/0210147 | A1 | 9/2006 | Sakaguchi |
| 2006/0253031 | A1 | 11/2006 | Altmann |
| 2007/0003123 | A1* | 1/2007 | Fu et al. ....................... 382/131 |
| 2007/0055142 | A1 | 3/2007 | Webler |
| 2007/0060833 | A1 | 3/2007 | Hauck |
| 2007/0167801 | A1 | 7/2007 | Webler et al. |
| 2007/0181139 | A1 | 8/2007 | Hauck |
| 2007/0223794 | A1 | 9/2007 | Preiss |
| 2007/0297657 | A1* | 12/2007 | Mattes .................. G06T 7/0081 382/128 |

FOREIGN PATENT DOCUMENTS

| | | |
|---|---|---|
| JP | 03-099630 | 4/1991 |
| JP | 1996-131403 | 5/1996 |
| JP | H08-131403 | 5/1996 |
| JP | 10-149445 | 6/1998 |
| JP | 2002-153443 | 5/2002 |
| JP | 2004-209262 | 7/2004 |
| JP | 2005-078176 | 3/2005 |
| JP | 2005-131367 | 5/2005 |
| WO | 1998/019619 | 5/1998 |
| WO | 2000/033723 | 6/2000 |
| WO | 2002/082375 | 10/2002 |
| WO | 2006/026177 | 3/2006 |
| WO | 2008/112420 | 9/2008 |

OTHER PUBLICATIONS

Chui et al., A new algorithm for non-rigid point matching, 2002, IEEE, vol. 2, pp. 44-51.*
Ju et al., Mean value coordinates for closed triangular meshes, Jul. 2005, ACM Trans on Graphics, vol. 24(3), pp. 561-566.*
Orr, Introduction to radial basis function networks, Apr. 1996.*
Ebeling et al., ASMOOTH: a simple and efficient algorithm for adaptive kernel smoothing of two-dimensional imaging data, 2006, vol. 368, pp. 65-73.*
Wiley, David F., "Evolutionary Morphing", Visualization, 2005, VIS 05. IEEE (Oct. 23-28, 2005), pp. 431-438.
U.S. Appl. No. 11/715,919, dated Mar. 9, 2007, Olson, et al.
Bookstein, FL., Principal Warps: Thin Plate Splines and the Decomposition of Deformations, IEEE Transactions on Pattern Analysis and Machine Intelligence, 11:567-585 (1989).
Bookstein, FL., Thin-Plate Splines and the Atlas Problem for Biomedical Images, Proceedings of the 12th International Conference on Information Processing in Medical Imaging (Jul. 1991). (abstract).
Schaefer & Warren, Mean Value Coordinates for Closed Triangular Meshes, ACM Transactions on Graphics, 24 (3):561-66 (Jul. 2005).
Park & Sanberg, "Universal approximation using radial-basis-function networks," Neural Computation, 3(2): 246-257 (1991). (abstract).
Bors & Pitas, "Median Radial Basis Function Neural Network," IEEE Trans, On Neural Networks, vol. 7, No. 6, pp. 1351-1364 (Nov. 1996).
Jain, A., K., et al., "FTRAC—A robust fluoroscope tracking fiducial" In Med. Phys. Oct. 2005, 32(10), p. 3185-3198 [retrieved on Aug. 9, 2008]. Retrieved from the internet: ,URL:http://custer.lcsr.jhu.edu/wiki/images/9/9E/jain05_B.PDF>.
Chui, H., et al., "A new algorithm for non-rigid point matching" In IEEE Conference on Computer Vision and Pattern Recognition, 2002, vol. 2, ISBN: 097695-0662-3, pp. 44-51. [retrieved on Aug. 9, 2008]. Retrieved from the internet: <URL: http://ieeexplore.ieee.org/xpl/.
Ju, T., et al., "Mean value coordinates for closed triangular meshes" In ACM Trans on Graphics, vol. 24(3), Jul. 2005, pp. 561-566 [retrieved on Aug. 9, 2008]. Retrieved from the internet: <URL: http://faculty.cs.tamu.edu/schaefer/research/meanvalue.pdf>.
Orr, M. J. L., "Introduction to radial basis function networks", Apr. 1996 [retrieved on Aug. 9, 2008]. Retrieved from the internet: <URL: http://www.lce.hut.fi/teachings/S-114.200/Orr_intro.ps.gz>.
Ebeling, H, et al., ? ASMOOTH: A simple and efficient algorithm for adaptive kernel smoothing of two-dimensional imaging data?, In Mon. Not. R. Astron. Soc. 2006, vol. 368, pp. 65-73 [retrieved on Aug. 9, 2008]. Retrieved from the internet: <URL: http/www.citebase.org/fulltext?format=application/pdf& identifier=oai:arXiv.org:astro-ph/0601306>.
International Search Report for PCT/US08/54969 Filed Feb. 26, 2008 and Written Opinion of International Searching Authority dated Aug. 15, 2008.
Supplementary European Search Report in EP Application No. EP 07870126.5 (dated Dec. 19, 2011).

(56) References Cited

OTHER PUBLICATIONS

Martin Auer et al., "An Automatic Nongrid Registration for Stained Histological Sections", IEEE Transactions on Image Processing, vol. 14, No. 4, pp. 475-486, Apr. 2005.
H.J. Johnson et al., "Consistent landmark and intensity-based image registration", IEEE Transactions on Medical Imaging, vol. 21, No. 5, May 2002, pp. 450-461.
K. Rohr et al., "Landmark-based elastic registration using approximating thin-plat splines", IEEE Transactions on Medical Imaging, vol. 20, No. 6, Jun. 2001,pp. 526-534.
M.A. Wirth et al., "Point-to-point registration of non-rigid medicei images local elastic transformation methods", Image Processing and its Applications, 1997, Sixth International Conference, vol. 2, Jul. 14, 1997, pp. 780-794.
Xian-yi cheng et al., "Design and realization of medical image nonrigid matching algorithm", Proceedings of the Sixth International Conference on Intelligent Systems Design and Applications (ISDA '06), Oct. 2006.
Supplementary European Search Report in EP Application No. 08730719.5 (dated May 16, 2012).
International Search Report and Written Opinion in PCT Application No. PCT/US2007/089198 (dated Jul. 22, 2008).
John Moody et al.; "Fat Learning in Networks of Locally-Tuned Procesing Units"; Neural Computation; vol. 1; No. 2; pp. 281-294; Jun. 1989.

\* cited by examiner

SYSTEM AND METHOD FOR LOCAL DEFORMABLE REGISTRATION OF A CATHETER NAVIGATION SYSTEM TO IMAGE DATA OR A MODEL

CROSS-REFERENCE TO RELATED APPLICATIONS

This application is related to U.S. application Ser. No. 11/715,919, filed 9 Mar. 2007, which is hereby incorporated by reference as though fully set forth herein.

BACKGROUND OF THE INVENTION a. Field of the Invention

The instant invention relates to localization systems, such as those used in cardiac diagnostic and therapeutic procedures. In particular, the instant invention relates to a system and method for registering the coordinate system of the localization system to the coordinate system of an externally generated model or image data set.

b. Background Art

It is known to generate a heart chamber geometry in preparation for cardiac diagnostic or therapeutic procedures. Often, a mapping catheter is introduced into the heart chamber of interest and moved around within the heart chamber, either randomly, pseudo-randomly, or according to one or more preset patterns, in order to capture a cloud of location points. The three-dimensional coordinates of the mapping catheter are typically measured using a localization system (sometimes also referred to as a "mapping system," "navigation system," or "positional feedback system"). The localization system measures the coordinates of the mapping catheter within a localization field, typically by relating a characteristic of the localization field, such as a voltage, experienced by the mapping catheter to a location of the catheter within the field. A surface model of the heart chamber geometry may then be generated by wrapping a surface around the cloud of location points.

In some instances, it is desirable to augment the localization system model of the heart chamber geometry with an external image or segmented model of the heart chamber. For example, it is known to utilize a CT or magnetic resonance image of a patient's heart to assist cardiologists or other clinicians in performing an electrophysiology study or cardiac ablation treatment. These three-dimensional images of the heart help the clinician to visualize the location of a medical device, such as an ablation catheter, within the patient's heart, thereby improving efficacy of treatment. Further, such three-dimensional images advantageously provide additional detail about the heart chamber geometry that may not be available with the model generated from the localization system standing alone.

The localization system may also be utilized to detect the position of another object, such as an electrophysiology or ablation catheter, within the localization field. It may be desirable to depict the position of the object, as measured by the localization system, on the three-dimensional image. However, the three-dimensional images typically do not utilize the same coordinate system as the localization system. Thus, the position of the object, as measured by the localization system, cannot be directly displayed on the three-dimensional image. Further, non-linearities and inhomogeneities in the localization field may introduce error if an affine transformation is used to transform the position of the object, as measured by the localization system, to a position on the three-dimensional image.

BRIEF SUMMARY OF THE INVENTION

It is desirable to be able to integrate an external three-dimensional model of cardiac geometry into a catheter navigation system.

It is further desirable to be able to provide a transformation that accurately transforms measurements of the catheter navigation system to positions on the external model.

It is also desirable that the transformation account for non-linearities and inhomogeneities in the catheter navigation system.

Disclosed herein is a method of registering a catheter navigation system, such as an electrical localization system or a magnetic localization system, to a three-dimensional image. The method includes the steps of: a) obtaining a three-dimensional image of at least a portion of a heart, the three-dimensional image including position information for a plurality of location points on a surface of the heart; b) placing a tool on a first surface location $X_1$ of the heart; c) measuring position information for the first surface location $X_1$; d) identifying a corresponding first location $Y_1$ on the three-dimensional image; e) associating the position information for the first surface location $X_1$ as measured by the catheter navigation system with position information for the corresponding first location $Y_1$ on the three-dimensional image as a fiducial pair $(X_1, Y_1)$; and f) using at least one fiducial pair to generate a mapping function that transforms points within the catheter navigation system to the three-dimensional image such that, for each fiducial pair $(X_i, Y_i)$, an error function measures a mapping error of about zero. The three-dimensional image may be selected from the group consisting of CT images, magnetic resonance images, ultrasound images, x-ray images, fluoroscopic images, image templates, localization system generated images, segmented models of any of the foregoing, and any combinations thereof.

In some embodiments of the invention, the step of identifying a corresponding first location $Y_1$ on the three-dimensional image includes: displaying a representation of the three-dimensional image on a display; and using an input device to identify the first location $Y_1$ on the representation of the three-dimensional image. Position information for the first surface location $X_1$ as measured by the catheter navigation system may thereafter be automatically associated with position information for the corresponding first location $Y_1$ as a fiducial pair $(X_1, Y_1)$. It is also contemplated that at least three, and, in some embodiments, at least four fiducial pairs may be associated.

A thin plate splines algorithm may be used to generate the mapping function. Typically, the thin plate splines algorithm will include summing a fixed number of weighted basis functions, wherein the number of weighted basis functions is the same as the number of fiducial pairs that were associated. If desired, the resulting mapping function may be smoothed with a regularization parameter, which is preferably about zero. Alternatively, a mean value coordinate algorithm may be used to generate the mapping function. In still other embodiments of the invention, a radial basis function networks algorithm may be used to generate the mapping function. Advantageously, the algorithm used compensates for inhomogeneities in the catheter navigation system such that, for each fiducial pair, there is a mapping error of about zero.

Optionally, the at least one fiducial pair may be smoothed prior to using the at least one fiducial pair to generate the mapping function. The at least one fiducial pair may be smoothed by using a kernel smoothing function. Alternatively, the at least one fiducial pair may be smoothed by: computing a rigid registration using the at least one fiducial pair, the rigid registration resulting in an error vector between members of the at least one fiducial pair; redefining the at least one fiducial pair by translating the members of the at least one fiducial pair closer together along the error vector resulting from the rigid registration; and using the redefined at least one fiducial pair to generate the mapping function.

Also disclosed is a method of registering a catheter navigation system to an n-dimensional image of a portion of a body of a patient, including the following steps: obtaining an n-dimensional image of a portion of a body of a patient including position information for a plurality of location points on a surface of the portion of the body; b) placing a tool on a surface location X of the portion of the body; c) measuring position information for the surface location X; d) identifying a corresponding location Y on the n-dimensional image; e) associating the measured position information for the surface location X with position information for the corresponding location Y on the three dimensional image as a fiducial pair (X, Y); f) repeating steps b) through e) to associate a plurality of fiducial pairs $(X_i, Y_i)$; and g) generating a function $f$ that maps points within an n-dimensional space of the catheter navigation system to an n-dimensional space of the n-dimensional image, wherein $|f(X_i)-Y_i|\approx 0$ for each of the plurality of fiducial pairs. The function $f$ may be generated using a thin plate splines algorithm, a mean value coordinates algorithm, a radial basis function networks algorithm, or another suitable warping algorithm.

In another aspect of the present invention, a method of registering a catheter navigation system to an image of at least a portion of a heart includes the following steps: determining position information for a location X relative to an n-dimensional space of a catheter navigation system; determining position information for a corresponding location Y relative to an n-dimensional space of an image of at least a portion of a heart; associating the position information for the location X with the position information for the corresponding location Y as a fiducial pair; and generating a mapping function $f$ that transforms points within the catheter navigation system to points within the image, such that, for each fiducial pair (X, Y), a divergence between $f(X)$ and Y is about zero.

The step of determining position information for a location X relative to a catheter navigation system optionally includes: obtaining a model of at least a portion of a heart, the model including position information for a plurality of location points on a surface of the heart measured relative to the catheter navigation system; displaying a representation of the model of at least a portion of the heart on a display; using an input device to identify the location X on the representation of the model of at least a portion of the heart; and determining position information for the location X identified on the representation of the model of at least a portion of the heart. Similarly, the step of determining position information for a corresponding location Y relative to an image of at least a portion of a heart optionally includes: obtaining an image of at least a portion of a heart, the image including position information for a plurality of location points on the surface of the heart measured relative to the image; displaying a representation of the image of at least a portion of the heart; using an input device to identify the location Y on the representation of the image of at least a portion of the heart; and determining position information for the location Y identified on the representation of the image of at least a portion of the heart, wherein the location X identified on the representation of the model of at least a portion of the heart and the location Y identified on the representation of the image of at least a portion of the heart correspond to a common location on the surface of the heart.

Alternatively, the step of determining position information for a location X relative to a catheter navigation system may include placing a catheter at the location X and using the catheter navigation system to measure position information for the location X. The catheter navigation system may measure position information for the location X based upon measurements of at least one characteristic of an electric field encountered at the location X or measurements of at least one characteristic of a magnetic field encountered at the location X.

According to another embodiment of the invention, a system for registering a catheter navigation system to an image of at least a portion of a heart generally includes: a catheter adapted to be inserted into at least a portion of a heart; a catheter navigation system adapted to place the catheter at a point X on the surface of the at least a portion of a heart and to measure position information for the point X on the surface of the at least a portion of a heart; an image of the at least a portion of a heart, the image including position information for a plurality of location points on the surface of the at least a portion of the heart; an input device coupled to the image of the at least a portion of a heart and adapted to permit a user to select a point Y on the image, wherein the selected point Y corresponds to the point X on the surface of the at least a portion of a heart at which the catheter is placed; a pairing processor programmed to associate the measured position information for the point X on the surface of the at least a portion of a heart at which the catheter is placed with position information for the selected point Y as a fiducial pair (X, Y); and a transform processor programmed to generate a mapping function $f$ that transforms points within an n-dimensional space of the catheter navigation system to points within an n-dimensional space of the image, such that, for each of a plurality of fiducial pairs (X, Y), a divergence between $f(X)$ and Y is about zero. The transform processor may be programmed with a thin plate splines algorithm, a mean value coordinates algorithm, a radial basis function networks algorithm, or another suitable warping algorithm.

In yet another embodiment of the invention, a system for registering a catheter navigation system to an image of at least a portion of a heart includes: an image of at least a portion of a heart, the image including n-dimensional position information for a plurality of location points on the surface of the at least a portion of the heart; a model of the at least a portion of the heart, the model including n-dimensional position information for a plurality of location points on the surface of the at least a portion of the heart measured relative to a catheter navigation system; an input device adapted to permit a user to select a point Y on the image of at least a portion of the heart and a point X on the model of the at least a portion of the heart; a pairing processor programmed to associate position information for the point Y selected on the image of at least a portion of the heart with position information for the point X selected on the model of the at least a portion of the heart as a fiducial pair (X, Y); and a transform processor programmed to generate a mapping function $f$ that transforms points within the catheter navigation system to points within the image, such that, for each of a plurality of fiducial pairs (X, Y), a divergence between $f(X)$ and Y is about zero. The point Y selected on the image of at least a portion of the heart and the point X selected on the model of the at least a portion of the heart preferably correspond to a common location on the surface of the at least a portion of the heart.

An advantage of the present invention is that it can be used to register a catheter navigation system to an external model such that the measurements made by the catheter navigation system may be given meaning relative to the external model.

Another advantage of the present invention is that it permits local deformable registration of the catheter navigation system to the external model, thereby compensating for non-linearities and inhomogeneities in the catheter navigation system.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a method and system for locally deformable registration of a catheter navigation system to an external model or external image data. That is, the present invention provides a method and system to transform the coordinate system of the catheter navigation system to the coordinate system of the external model or external image data. Thus, the term "external" refers to a model or image data using a different coordinate system than the catheter navigation system. The phrase "external image" will be used throughout the specification to refer to the external model or external image data to which the catheter navigation system is registered. Preferably, the external image includes position information for a plurality of location points. Typically, the position information will be expressed as a Cartesian coordinate within the coordinate system of the external image, though the use of other coordinate systems, such as polar, spherical, and cylindrical, is also contemplated.

Typical external images include, without limitation, CT images, magnetic resonance images, ultrasound images, x-ray images, and fluoroscopic images. It is also contemplated that the external image may be an image template rather than an image specific to a particular patient. Further, it is also within the scope of the invention for the external image to be an image generated from position data collected by a localization system. As one of ordinary skill in the art will appreciate, such data is external, as that term is used herein, if it is measured relative to a different origin. Thus, it may come from a different localization system, or from the same localization system relative to a different reference (e.g., localization system data collected during an earlier procedure or measured relative to different electrodes). The external image may be segmented or unsegmented, and may also be derived from another suitable source.

Though the present invention will be described in connection with cardiac procedures, and more particularly in connection with a procedure carried out in a heart chamber, it is contemplated that the present invention may be practiced to good advantage in other contexts. Further, though the present invention will generally be described in three dimensions, one of ordinary skill in the art will understand how to apply the principles disclosed herein in any number of dimensions.

Figure 1:
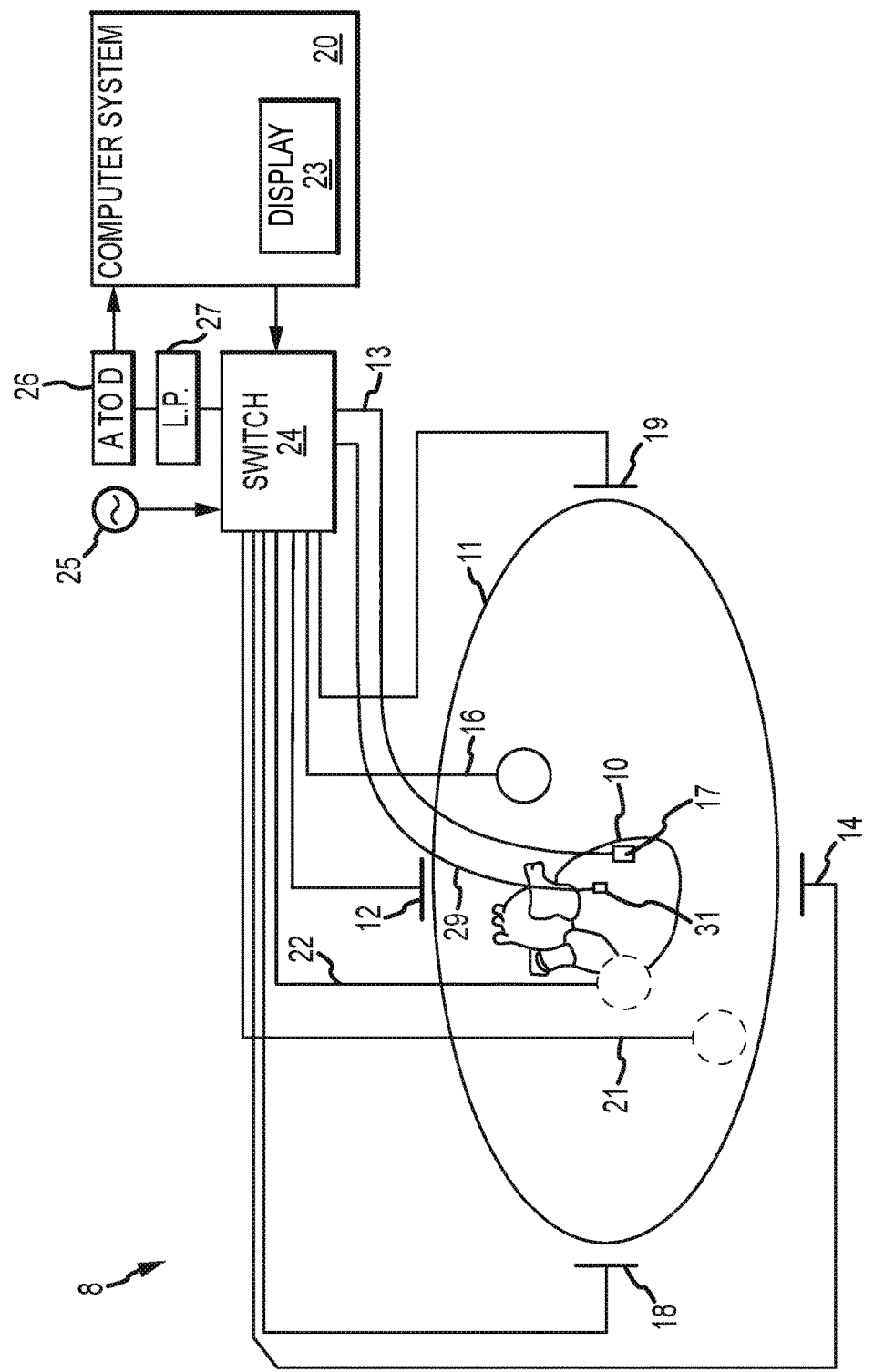
FIG. 1 is a schematic diagram of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. Three sets of surface electrodes (e.g., patch electrodes) are shown applied to a surface of the patient 11, defining three generally orthogonal axes, referred to herein as an x-axis, a y-axis, and a z-axis. The x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram (ECG) system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

Figure 2:
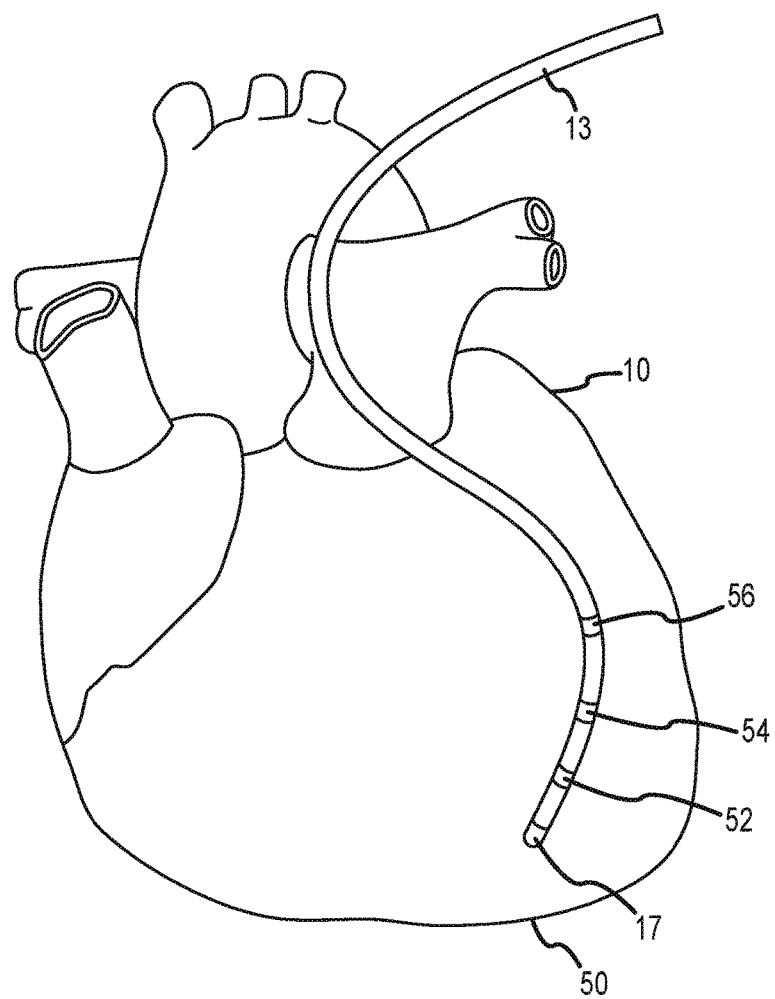
FIG. 2 depicts an exemplary catheter used in an electrophysiology study.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional measurement electrodes 52, 54, 56 spaced along its length. Since each of these electrodes 17, 52, 54, 56 lies within the patient, location data may be collected simultaneously for each of the electrodes by localization system 8.

One suitable system for navigating catheter 13 through patient 11 is the robotic surgical system disclosed in U.S. application Ser. No. 11/647,272, filed 29 Dec. 2006 ("the '272 application"), which is hereby expressly incorporated by reference as though fully set forth herein. Of course, other mechanical, electromechanical, or robotic systems may be utilized to navigate catheter 13 through patient 11 without departing from the spirit and scope of the present invention. In addition, it is contemplated that, in some embodiments of the invention, catheter 13 may be manually manipulated through patient 11.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. Preferably, the coordinate system is a three-dimensional (x, y, z) Cartesian coordinate system, though the use of other coordinate systems, such as polar, spherical, and cylindrical coordinate systems, is within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Patent Application Publication No. 2004/0254437, which is hereby incorporated herein by reference in its entirety. The electrode data may also be used to compensate for changes in the impedance of the body of the patient as described in co-pending U.S. application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite Nav™ navigation and visualization system of St. Jude Medical, Atrial Fibrillation Division, Inc., which generates the electrical fields described above. Other localization systems, however, may be used in connection with the present invention, including for example, the CARTO navigation and location system of Biosense Webster, Inc. and the AURORA® system of Northern Digital Inc., both of which utilize magnetic localization fields rather than electrical localization fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether electrical fields (e.g., EnSite Nav™), magnetic fields (e.g., CARTO), or other suitable fields, may be referred to generically as "localization fields," while the elements generating the fields, such as surface electrodes 12, 14, 16, 18, 19, and 22 may be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56), and thereby determine position information for the roving electrodes 17, 52, 54, and 56. Though the present invention will be described primarily in the context of a localization system that generates an electrical field, one of ordinary skill in the art will understand how to apply the principles disclosed herein in other types of localization fields (e.g., by replacing electrodes 17, 52, 54, 56 with coils to detect different components of a magnetic field).

As should be clear from the foregoing discussion, the position information measured by localization system 8 is context-specific to the localization system 8. That is, it describes the position of roving electrodes 17, 52, 54, and 56 relative to the coordinate system of localization system 8. It is desirable to integrate the position information measured by localization system 8 with an external image such that the position information measured by localization system 8 may be mapped to the external image, which, as described above, utilizes a different coordinate system than localization system 8. This is referred to as "registering" localization system 8 to the external image. Once localization system 8 has been registered to the external image, the position of electrodes 17, 52, 54, and 56, as measured by localization system 8 relative to the coordinate system of localization system 8, can be accurately and precisely illustrated on the external image relative to the coordinate system of the external image.

Figure 3:
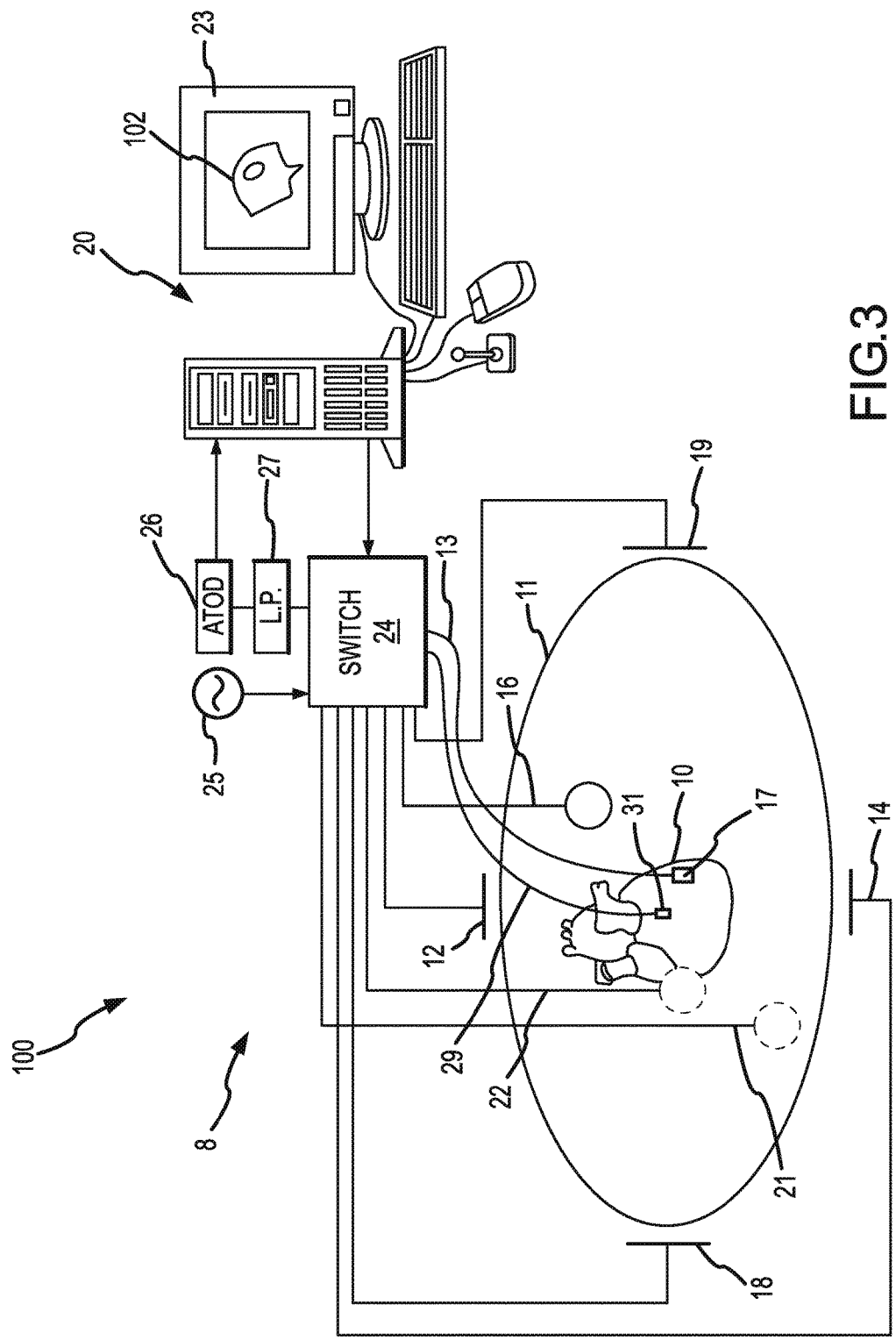
FIG. 3 schematically illustrates a system for registering a catheter navigation system to a three-dimensional image.

A method of registering a catheter navigation system (e.g., localization system 8) to a three-dimensional image will be described with reference to FIG. 3, which schematically depicts a system 100 for registering a catheter navigation system to a three-dimensional image. A three-dimensional external image of the heart chamber is obtained, for example by retrieving the external image from a storage medium such as a hard disk, optical disk, or memory that may be part of computer system 20. As described above, the external image may be generated using CT, magnetic resonance, ultrasound, x-ray, fluoroscopy, or another suitable imaging or modeling technique, or may be an image template rather than an image specific to a particular patient. Preferably, the external image includes position information for a plurality of location points on the surface of the heart chamber. Once the external image is obtained, a representation 102 thereof may be displayed on display 23.

A tool (e.g., catheter 13) may then be placed on a first surface location $X_1$ of the heart chamber, for example by robotically navigating catheter 13 into contact with the surface of the heart chamber using the contact-sensing robotic surgical system disclosed in the '272 application or by manually bringing catheter 13 into contact with the surface of the heart chamber. Position information for the first surface location $X_1$ may be measured using localization system 8 as described above (e.g., by measuring at least one characteristic of an electric field or magnetic field at the first surface location $X_1$). This position information is preferably expressed as an (x, y, z) coordinate measured relative to the origin of localization system 8 (e.g., reference electrode 31).

The user then identifies a point $Y_1$ on the three-dimensional external image that corresponds to the first surface location $X_1$ on the surface of the heart chamber. Various imaging techniques, such as fluoroscopy and intracardiac echo (ICE), may be used to aid the user in visualizing the location of catheter 13 on the surface of the heart chamber, thereby simplifying the task of identifying $Y_1$ on the external image. A readily-identifiable anatomical feature and/or the physician's experience and expertise may also be used to verify correspondence between $X_1$ and $Y_1$. For example, if the physician's experience indicates that the first surface location $X_1$ on the surface of the heart chamber is adjacent to the mitral valve, the physician will then identify a point $Y_1$ on the three-dimensional external image that is adjacent to the mitral valve.

In some embodiments of the invention, the first location $Y_1$ is identified by using an input device to identify, or "pick," the first location $Y_1$ on representation 102 of the three-dimensional external image as displayed on display 23. Suitable input devices include, without limitation, keyboards, keypads, pointing devices (e.g., mice, trackballs, and trackpads), two- and three-dimensional joysticks, and active and passive touch-sensitive displays. Preferably, the first location $Y_1$ will have position information expressed as an (x, y, z) coordinate measured relative to the three-dimensional external image.

Figure 4:
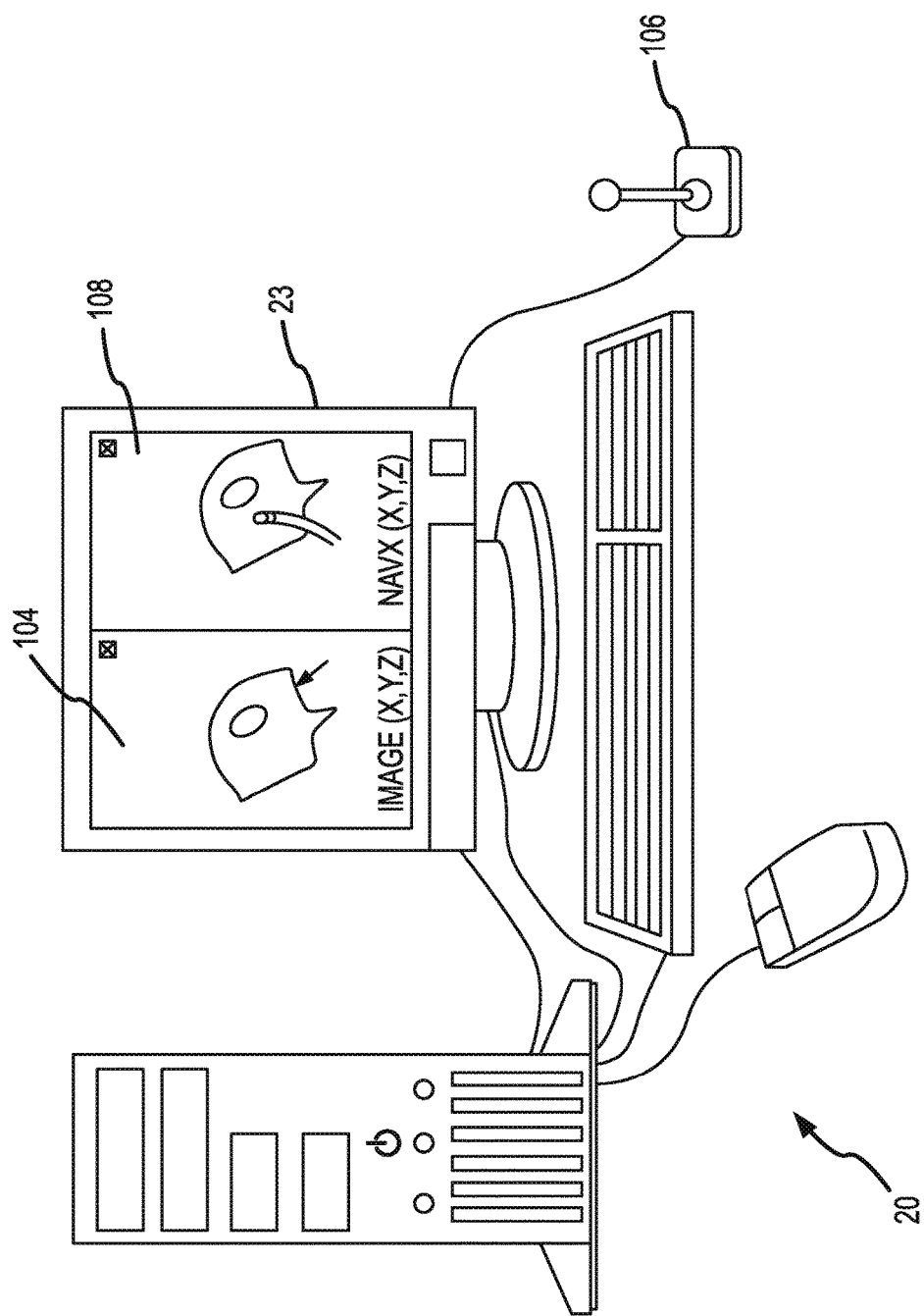
FIG. 4 illustrates an exemplary graphical user interface that may be used in registering a catheter navigation system to a three-dimensional image.

FIG. 4 illustrates an exemplary graphical user interface (GUI) that may be used in practicing the present invention. Representation 102 of the three-dimensional external image is shown in a window 104. A three-dimensional joystick 106 (e.g., a joystick with three input axes) is used to point and click on the first location $Y_1$ on representation 102. To aid the user in visualizing correspondence between $X_1$ and $Y_1$, a second window 108 may depict catheter 13 within the heart chamber, for example by displaying a fluoroscopic or ICE image or a model generated from data collected by localization system 8. By observing the position of catheter 13 within the heart chamber in second window 108, the user can identify the corresponding point $Y_1$ on representation 102 displayed in window 104. It is within the spirit and scope of the present invention, however, to graphically display only representation 102 in window 104, relying upon the physician's expertise and experience rather than imagery in identifying the first surface location $X_1$.

A fiducial pair $(X_1, Y_1)$ is then created by associating the position information for the first surface location $X_1$, as measured by localization system 8, with the position information for the corresponding first location $Y_1$ on the three-dimensional external image. In some embodiments of the invention, a pairing processor, which may be incorporated into computer system 20, automatically associates the measured position information for first surface location $X_1$ with the position information for the picked point $Y_1$. Thus, the fiducial pair $(X_1, Y_1)$ is a pair of (x, y, z) coordinates, one measured relative to the origin of localization system 8 and one measured relative to the origin of the three-dimensional external image. Multiple fiducial pairs $(X_i, Y_i)$ may be associated using a similar place-and-pick process.

The methodology described above can be referred to generally as a "single pick" implementation, in that the user of system 100 is required only to pick the point $Y_i$ on the external image (e.g., representation 102 in window 104). Position information for the other element of the fiducial pair, the surface location $X_i$, is determined by measuring the position of catheter 13 relative to localization system 8, and may be automatically associated with the position information for the corresponding point $Y_i$ picked by the user.

It is also contemplated, however, to utilize a "dual pick" implementation. That is, rather than measuring the position of catheter 13 relative to localization system 8 to determine position information for the point $X_i$, a pick process may be utilized to select the location $X_i$ relative to localization system 8. For example, referring again to FIG. 4, second window 108 may display a representation of a surface model of the heart chamber generated by localization system 8, including position information for a plurality of location points on the surface of the heart measured relative to localization system 8. Rather than, or in addition to, manipulating catheter 13 into position, the user may utilize three-dimensional joystick 106 to pick location $X_i$, for example a point adjacent the mitral valve, on the representation shown in second window 108. The user may then toggle over to window 104 to pick corresponding location $Y_i$ on representation 102 of the external image. Position information for both $X_i$ and $Y_i$ may be determined, respectively, from the surface model and the external image, and associated as a fiducial pair $(X_i, Y_i)$. Of course, this dual pick methodology may be repeated multiple times in order to associate multiple fiducial pairs.

As one of ordinary skill in the art should appreciate, the fiducial pairs may be used to generate a mapping function $f$ that registers localization system 8 to the three-dimensional image. That is, the mapping function $f$ can be used to transform position information expressed according the coordinate system of localization system 8 to position information expressed according to the coordinate system of the three-dimensional image.

For a linear and homogeneous localization system 8, an affine transformation (e.g., translation, rotation, and scaling), such as would result from application of a least mean square error fit, would be suitable. Many localization systems, however, are non-linear and homogeneous, such that an affine transformation may not precisely align the coordinate system of localization system 8 with the coordinate system of the external image. Preferably, therefore, a mapping function is used that locally warps the coordinate system of localization system 8 to force an exact match to the coordinate system of the three-dimensional external image at each fiducial pair, thereby compensating for non-linearities and inhomogeneities in localization system 8. That is, for each fiducial pair $(X_i, Y_i)$, an error function e preferably measures a mapping error (e.g., a divergence between $f(X_i)$ and $Y_i$) of about zero. This can be expressed as $e \equiv |f(X_i) - Y_i| \approx 0$. In some embodiments of the invention, a suitably programmed transform processor incorporated into computer system 20 generates the mapping function $f$.

There are a number of suitable warping algorithms for generating the mapping function $f$. One preferred algorithm is the thin plate splines algorithm, which is known for use in fusing images from distinct modalities (e.g., PET with CT) or to register new image data to image atlases. Generally, the thin plate splines algorithm includes summing a fixed number of weighted basis functions. Typically, the number of weighted basis functions will be equal to the number of fiducial pairs. The following articles, which are hereby incorporated by reference as though fully set forth herein, describe the thin plate splines algorithm in further detail:

Bookstein, F L. Principal Warps: Thin Plate Splines and the Decomposition of Deformations. *IEEE Transactions on Pattern Analysis and Machine Intelligence*. 1989. 11:567-585.

Bookstein, F L. Thin-Plate Splines and the Atlas Problem for Biomedical Images. *Proceedings of the 12th International Conference on Information Processing in Medical Imaging*. July, 1991.

It is also contemplated that the thin plate splines algorithm may also utilize a regularization parameter $\lambda$, preferably of about zero, to smooth the resultant mapping function. One of ordinary skill would appreciate and understand how to apply a regularization parameter to smooth the mapping function.

Another suitable warping algorithm is a mean value coordinates algorithm. A mean value coordinates algorithm generally transforms individual points in three dimensions to a closed, triangulated surface in three dimensions known as a "control mesh." When the control mesh is deformed, the algorithm can compute a smooth interpolation function through three-dimensional space that exactly deforms the vertices and triangles without wildly extrapolating in regions far from the control mesh. The following article, which is hereby incorporated by reference as though fully set forth herein, describes mean value coordinates algorithms in further detail: Ju T, Schaefer S, Warren J, Mean Value Coordinates for Closed Triangular Meshes. *ACM Transactions on Graphics*. July 2005. 24(3):561-66.

In some embodiments of the invention, the fiducial pairs of (x, y, z) coordinates are the vertices of the control mesh, which deforms from the three-dimensional space of localization system 8 to the three-dimensional space of the external image. The vertices are connected with a two-dimensional Delaunay triangulation, for example by projecting them onto a sphere centered at their centroid and computing the convex hull. Such a process will include all the vertices, and the triangulation is close to optimal when the fiducial pairs are well-distributed on the endocardial surface of the heart chamber. The mean value coordinates algorithm then uses the control and deformed meshes to efficiently and smoothly transform any (x, y, z) coordinate from the coordinate system of localization system 8 to the coordinate system of the external image.

Still another suitable warping algorithm is the radial basis function networks algorithm, which is well known in neural networks. The following articles and books describe radial basis function networks algorithms in further detail, and are hereby incorporated by reference as though fully set forth herein.

J. Moody and C. J. Darken, "Fast learning in networks of locally tuned processing units," Neural Computation, 1, 281-294 (1989).

J. Park and I. W. Sandberg, "Universal approximation using radial-basis-function networks," Neural Computation, 3(2): 246-257 (1991).

A. G. Bors and I. Pitas, "Median Radial Basis Function Neural Network," IEEE Trans. On Neural Networks, vol. 7, no. 6, pp. 1351-1364 (November 1996).

Martin D. Buhmann and M. J. Ablowitz, "Radial Basis Functions: Theory and Implementations," Cambridge University (2003).

Paul V. Yee and Simon Haykin, "Regularized Radial Basis Function Networks: Theory and Applications," John Wiley (2001).

Though any number of fiducial pairs may be utilized to generate the mapping function $f$, it is preferable to use at least three fiducial pairs $(X_1, Y_1)$, $(X_2, Y_2)$, and $(X_3, Y_3)$, and more preferably at least four fiducial pairs $(X_1, Y_1)$, $(X_2, Y_2)$, $(X_3, Y_3)$, and $(X_4, Y_4)$, to generate the mapping function. The use of one, two, or three fiducial pairs will result in a rigid registration of localization system 8 to the three-dimensional external image. On the other hand, four or more fiducial pairs will permit a deformable registration of localization system 8 to the three-dimensional external image, which is desirable where localization system 8 is non-linear. Further, it should be understood that additional fiducial pairs will improve the mapping function $f$, and therefore will improve the efficacy of the registration of localization system 8 to the external image.

It is also contemplated that the mapping function may be regularized by smoothing the input data—the fiducial pairs—before the mapping function is generated through application of a suitable warping algorithm as described above. In some embodiments of the invention, a kernel smoothing function is utilized to smooth the input data. One suitable kernel function is a derivative of a Gaussian curve, and may be given by the general formula $$K(x) = ae^{-\frac{x^2}{2\sigma^2}}.$$

It is contemplated, however, that any kernel function having a central maximum and a smooth decay to zero as distance from the central maximum increases may be utilized to practice the present invention. The input data may be smoothed by computing a weighted sum of all the Y fiducial points based on the distance from the X fiducial point being smoothed according to the kernel function. (As described above, the X and Y points are the points that define the fiducial pair.) In the general formula given above, x is the distance from each X fiducial point to the X location of the fiducial point being smoothed.

Other methods of smoothing the fiducial point pairs are also possible. One such method would be to first compute the optimal rigid registration for the fiducial pairs. For each fiducial pair, there would be a residual error vector remaining after this computation. A new set of fiducial pairs can be generated by moving the original fiducial points closer together along this vector. Using the new, modified set of fiducial pairs, the deformable registration may be computed. If the fiducial points are moved the full distance along the error vector, such that the members of the fiducial pair are located at an identical position, the result will be a registration equivalent to the rigid registration. If the members of the fiducial pair are not moved, the result will be a registration equivalent to what would be achieved if the deformable registration was computed on the original fiducial points immediately. By adjusting the percentage by which the members of the fiducial pair are translated along the error vectors, different levels of smoothing may be achieved.

The methods described above may be executed by one or more computer systems, and may be software implemented (e.g., one or more software programs executed by one or more computer systems or processors), hardware implemented (e.g., a series of instructions stored in one or more solid state devices), or a combination of both. As described above, the computer may be a conventional general purpose computer, a special purpose computer, a distributed computer, or any other type of computer. Further, the computer may comprise one or more processors, such as a single central processing unit or a plurality of processing units, commonly referred to as a parallel processing environment. The term "processor" as used herein refers to a computer microprocessor and/or a software program (e.g., a software module or separate program) that is designed to be executed by one or more microprocessors running on one or more computer systems. By way of further example, each of the processes described herein can be implemented using one or more computer processors running on one or more computer systems, thereby establishing a computerized system and method for the present invention.

Although several embodiments of this invention have been described above with a certain degree of particularity, those skilled in the art could make numerous alterations to the disclosed embodiments without departing from the spirit or scope of this invention. For example, it is within the spirit and scope of the present invention to associate a fiducial pair by navigating catheter 13 to a corresponding location on the surface of the heart chamber in response to a prompt depicted on representation 102 of the external model. Similarly, it is contemplated that catheter 13 may be positioned to a plurality of locations on the surface of the heart chamber, which locations may then be used to generate a surface model of the heart chamber. The plurality of locations may then be "played back," and the user may select the corresponding point on the external image as each location is played back. It is also contemplated that image modalities may be registered to each other according to the methods and system disclosed herein (e.g., registering a CT image to a magnetic resonance image or a CT image to a model generated by a catheter navigation system).

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of registering a catheter navigation system to a three-dimensional image, comprising:
    a) obtaining a three-dimensional image of at least a portion of a heart, the three-dimensional image including position information for a plurality of location points on a surface of the heart measured relative to a coordinate frame Y;
    b) placing a tool on a surface location $X_i$ of the heart;
    c) measuring position information for the surface location $X_i$ relative to a coordinate frame X;
    d) identifying a corresponding location $Y_i$ on the three-dimensional image;
    e) associating the position information for the surface location $X_i$ as measured by the catheter navigation system relative to the coordinate frame X with position information for the corresponding location $Y_i$ on the three-dimensional image relative to the coordinate frame Y as a fiducial pair $(X_i, Y_i)$; and
    f) using at least two fiducial pairs $(X_i, Y_i)$ to generate a mapping function $f$ that transforms points within the coordinate frame X the to coordinate frame Y such that, for each fiducial pair $(X_i, Y_i)$, an error function $f(X_i)-Y_i \approx 0$, wherein the step of using the at least two fiducial pairs to generate a mapping function comprises:
    using a thin plate splines algorithm to generate the mapping function,
    wherein the thin plate splines algorithm comprises summing a fixed number of weighted basis functions,
    wherein the fixed number of weighted basis functions is the same as a number of fiducial pairs that were associated, and
    wherein the mapping function compensates for inhomogeneities in the catheter navigation system such that, for each fiducial pair $(X_i, Y_i)$, the error function $f(X_i)-Y_i \approx 0$.

2. The method of claim 1, further comprising smoothing the mapping function with a regularization parameter.

3. The method of claim 2, wherein the regularization parameter is about zero.

4. A method of registering a catheter navigation system to a three-dimensional image, comprising:

a) obtaining a three-dimensional image of at least a portion of a heart, the three-dimensional image including position information for a plurality of location points on a surface of the heart measured relative to a coordinate frame Y;
b) placing a tool on a surface location $X_i$ of the heart;
c) measuring position information for the surface location $X_i$ relative to a coordinate frame X;
d) identifying a corresponding location $Y_i$ on the three-dimensional image;
e) associating the position information for the surface location $X_i$ as measured by the catheter navigation system relative to the coordinate frame X with position information for the corresponding location $Y_i$ on the three-dimensional image relative to the coordinate frame Y as a fiducial pair $(X_i, Y_i)$; and
f) using at least two fiducial pairs $(X_i, Y_i)$ to generate a mapping function $f$ that transforms points within the coordinate frame X to the coordinate frame Y such that, for each fiducial pair $(X_i, Y_i)$, an error function $f(X_i)-Y_i \approx 0$, wherein the step of using the at least two fiducial pairs to generate a mapping function comprises using a mean value coordinate algorithm to generate the mapping function, wherein the mean value coordinate algorithm compensates for inhomogeneities in the catheter navigation system such that, for each fiducial pair $(X_i, Y_i)$, the error function $f(X_i)-Y_i \approx 0$.

5. The method of claim 4, further comprising:
repeating steps b) through e) until at least four fiducial pairs are associated; and
generating a closed triangulated surface model of at least a portion of the heart, wherein the vertices of the closed triangulated surfaces comprise the at least four fiducial pairs.

6. A method of registering a catheter navigation system to a three-dimensional image, comprising:
a) obtaining a three-dimensional image of at least a portion of a heart, the three-dimensional image including position information for a plurality of location points on a surface of the heart measured relative to a coordinate frame Y;
b) placing a tool on a surface location $X_i$ of the heart;
c) measuring position information for the surface location $X_i$ relative to a coordinate frame X;
d) identifying a corresponding location $Y_i$ on the three-dimensional image;
e) associating the position information for the surface location $X_i$ as measured by the catheter navigation system relative to the coordinate frame X with position information for the corresponding location $Y_i$ on the three-dimensional image relative to the coordinate frame Y as a fiducial pair $(X_i, Y_i)$; and
f) using at least two fiducial pairs $(X_i, Y_i)$ to generate a mapping function $f$ that transforms points within the coordinate frame X to the coordinate frame Y such that, for each fiducial pair $(X_i, Y_i)$, an error function $f(X_i)-Y_i \approx 0$, wherein the step of using the at least two fiducial pairs to generate a mapping function comprises using at least three fiducial pairs and a mean value coordinate algorithm to generate the mapping function, wherein the mean value coordinate algorithm compensates for inhomogeneities in the catheter navigation system such that, for each fiducial pair $(X_i, Y_i)$, the error function $f(X_i)-Y_i \approx 0$.

7. A method of registering a catheter navigation system to a three-dimensional image, comprising:
a) obtaining a three-dimensional image of at least a portion of a heart, the three-dimensional image including position information for a plurality of location points on a surface of the heart measured relative to a coordinate frame Y;
b) placing a tool on a surface location $X_i$ of the heart;
c) measuring position information for the surface location $X_i$ relative to a coordinate frame X;
d) identifying a corresponding location $Y_i$ on the three-dimensional image;
e) associating the position information for the surface location $X_i$ as measured by the catheter navigation system relative to the coordinate frame X with position information for the corresponding location $Y_i$ on the three-dimensional image relative to the coordinate frame Y as a fiducial pair $(X_i, Y_i)$; and
f) using at least two fiducial pairs $(X_i, Y_i)$ to generate a mapping function $f$ that transforms points within the coordinate frame X to the coordinate frame Y such that, for each fiducial pair $(X_i, Y_i)$, an error function $f(X_i)-Y_i \approx 0$, wherein the step of using the at least two fiducial pairs to generate a mapping function comprises using a radial basis function networks algorithm to generate the mapping function, wherein the radial basis function networks algorithm compensates for inhomogeneities in the catheter navigation system such that, for each fiducial pair $(X_i, Y_i)$, the error function $f(X_i)-Y_i \approx 0$.

8. The method according to claim 1, wherein the tool comprises a catheter including at least one localization element that can be localized by the catheter navigation system.

9. The method according to claim 8, further comprising:
g) localizing the at least one localization element within the coordinate frame X using the catheter navigation system;
h) transforming the localization of the at least one localization element into the coordinate frame Y using the mapping function $f$, and i) depicting a graphical representation of the tool in the three-dimensional image of at least a portion of a heart.

* * * * *